United States Patent [19]

Wollweber et al.

[11] Patent Number: 4,965,275

[45] Date of Patent: Oct. 23, 1990

[54] PESTICIDAL PYRIDINE-4-CARBOXYLIC ACID ANILIDES

[75] Inventors: Detlef Wollweber, Wuppertal; Wolfgang Krämer, Burscheid; Stefan Dutzmann, Duesseldorf; Wilhelm Brandes, Leichlingen, all of Fed. Rep. of Germany

[73] Assignee: Bayer Aktiengesellschaft, Leverkusen, Fed. Rep. of Germany

[21] Appl. No.: 316,056

[22] Filed: Feb. 24, 1989

[30] Foreign Application Priority Data

Mar. 1, 1988 [DE] Fed. Rep. of Germany ....... 3806489

[51] Int. Cl.$^5$ ................... C07D 213/81; A01N 43/40
[52] U.S. Cl. ........................................ 514/354; 546/2; 546/8; 546/323; 546/283
[58] Field of Search ................. 546/323, 2, 8; 514/354

[56] References Cited

U.S. PATENT DOCUMENTS 4,377,407  3/1983  Shirakawa et al. ..................... 71/76

Primary Examiner—Alan L. Rotman
Attorney, Agent, or Firm—Spring, Horn, Kramer & Woods

[57] ABSTRACT

Fungicidal pyridine-4-carboxylic acid anilides of the formula

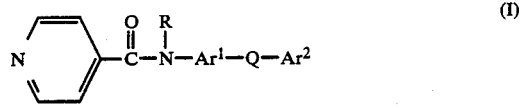
(I)

in which
R stands for hydrogen or alkyl,
Q stands for a radical of the formula

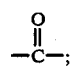

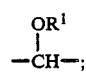

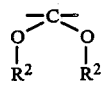

or

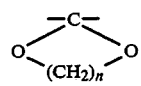

where
$R^1$ stands for hydrogen or alkyl,
$R^2$ stands for alkyl and
n stands for a number 2, 3 or 4,
$Ar^1$ stands for an optionally substituted o-phenylene radical and
$Ar^2$ stands for optionally substituted phenyl, with the proviso that at least one of the radicals $Ar^1$ or $Ar^2$ substituted by halogenoalkoxy or halogenoalkylthio,
and acid addition salts and metal salt complexes thereof.

8 Claims, No Drawings

PESTICIDAL PYRIDINE-4-CARBOXYLIC ACID ANILIDES

The invention relates to new pyridine-4-carboxylic acid anilides, several processes for their preparation and their use as pest-combating agents.

It is known that certain pyridine-4-carboxylic acid anilides, such as for example the compound N-[4-chloro-2-(4-chloro-α,α-diethoxybenzyl)-phenyl]-pyridine-4-carboxamide or the compound N-[2-(4-chlorobenzoyl)phenyl]-pyridine-4-carboxamide or the compound N-[2-(4-chloro-α-hydroxybenzyl)-phenyl]-pyridine-4-carboxamide or the compound N-[2-(4-chloro-α,α-diethoxybenzyl)phenyl]-pyridine-4-carboxamide possess fungicidal activity (compare, for example, EP No. 122,410; Jpn. Kokai Tokkyo Koho No. Jp 60/32,703; Jpn. Kokai Tokkyo Koho No. Jp 60/23,364).

However, the activity of these previously known compounds is not completely satisfactory in all areas of use, in particular at low application rates and concentrations.

New pyridine-4-carboxylic acid anilides of the general formula (I)

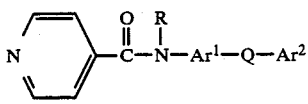  (I)

in which
R stands for hydrogen or alkyl,
Q stands for a radical of the formula

or

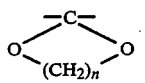

where
R¹ stands for hydrogen or alkyl,
R² stands for alkyl and
n stands for a number 2, 3 or 4,
Ar¹ stands for an optionally substituted o-phenylene radical and
Ar² stands for optionally substituted phenyl, with the proviso that at least one of the radicals Ar¹ or Ar² is substituted by halogenoalkoxy or halogenoalkylthio, and their acid addition salts and metal salt complexes have been found.

Furthermore, it has been found that the new pyridine-4-carboxylic acid anilides of the formula (I)

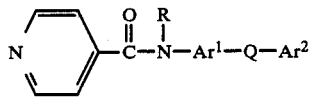  (I)

in which
R stands for hydrogen or alkyl,
Q stands for a radical of the formula

or

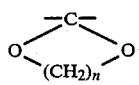

where
R¹ stands for hydrogen or alkyl,
R² stands for alkyl and
n stands for a number 2, 3 or 4,
Ar¹ stands for an optionally substituted o-phenylene radical and
Ar² stands for optionally substituted phenyl, with the proviso that at least one of the radicals Ar¹ or Ar² is substituted by halogenoalkoxy or halogenoalkylthio, and their acid addition salts and metal salt complexes are obtained according to one of the processes described in the following:

(a) pyridine-4-carboxylic acids of the formula (Ia)

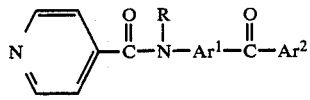  (Ia)

in which R, Ar¹ and Ar² have the abovementioned meaning,
are obtained when pyridine-4-carbonyl halide hydrochlorides of the formula (II)

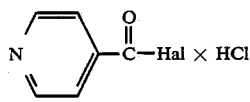  (II)

in which Hal stands for halogen, such as fluorine, chlorine or bromine, preferably for chlorine,
are reacted with aminobenzophenones of the formula (III)

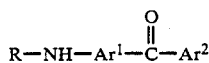  (III)

in which R, Ar¹ and Ar² have the abovementioned meaning, if appropriate in the presence of a diluent and if appropriate in the presence of an acid-binding agent; (b) pyridine-4-carboxylic acid anilides of the formula (Ib)

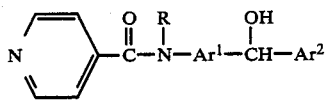
(Ib)

in which R, $Ar^1$ and $Ar^2$ have the abovementioned meaning,
are obtained when the pyridine-4-carboxylic acid anilides of the formula (Ia)

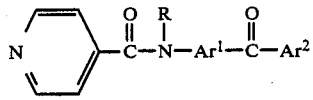
(Ia)

in which R, $Ar^1$ and $Ar^2$ have the abovementioned meaning,
obtainable with the aid of process (a) are reacted with reductants if appropriate in the presence of a diluent;

(c) pyridine-4-carboxylic acid anilides of the formula (Ic)

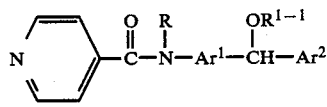
(Ic)

in which $R^{1-1}$ stands for alkyl and R, $Ar^1$ and $Ar^2$ have the abovementioned meaning,
are obtained when the pyridine-4-carboxylic acid anilides of the formula (Ib)

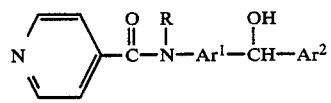
(Ib)

in which R, $Ar^1$ and $Ar^2$ have the abovementioned meaning,
obtainable with the aid of process (b), are reacted with alkylating agents of the formula (IV)

(IV)

in which $R^{1-1}$ has the abovementioned meaning and E stands for an electron-withdrawing leaving group,
if appropriate in the presence of a diluent and if appropriate in the presence of a reaction auxiliary;

(d) pyridine-4-carboxylic acid anilides of the formula (Id)

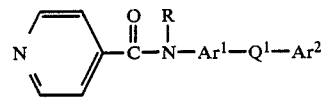
(Id)

in which $Q^1$ stands for a radical of the formula

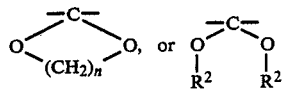

where
$R^2$ and n have the abovementioned meaning,
are obtained when the pyridine-4-carboxylic acid anilides of the formula (Ia)

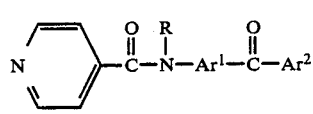
(Ia)

in which R, $Ar^1$ and $Ar^2$ have the abovementioned meaning,
obtainable with the aid of process (a) are reacted with at least 2 moles of alcohol or at least 1 mole of diol of the formula (V)

HO—$R^3$ (V)

in which $R^3$ stands for alkyl or for a radical —$(CH_2)_n$—OH, where n has the abovementioned meaning,
if appropriate in the presence of a diluent and if appropriate in the presence of a reaction auxiliary and if appropriate an acid or a metal salt is subsequently adducted.

Finally, it has been found that the new pyridine-4-carboxylic acid anilides of the general formula (I) and their acid addition salts and metal salt complexes possess a good activity against pests.

Surprisingly, the pyridine-4-carboxylic acid anilides of the general formula (I) according to the invention show, for example, a considerably better fungicidal activity than the pyridine-4-carboxylic acid anilides known from the prior art, such as, for example, the compound N-[4-chloro-2-(4-chloro-α,α-diethoxybenzyl)-phenyl]-pyridine-4-carboxamide or the compound N-[2-(4-chlorobenzoyl)-phenyl]-pyridine-4-carboxamide or the compound N-[2-(4-chloro-α-hydroxybenzyl)-phenyl]-pyridine-4-carboxamide or the compound N-[2-(4-chloro-α,α-diethoxybenzyl)-phenyl]-pyridine-4-carboxamide, which are related compounds chemically and with respect to their action.

Formula (I) provides a general definition of the pyridine-4-carboxylic acid anilides according to the invention. Preferred compounds of the formula (I) are those in which
R stands for hydrogen or for straight-chain or branched alkyl having 1 to 4 carbon atoms,
Q stands for a radical of the formula

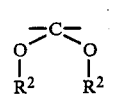

or

-continued

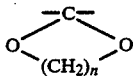

where
R¹ stands for hydrogen or for straight-chain or branched alkyl having 1 to 4 carbon atoms,
R² stands for straight-chain or branched alkyl having 1 to 4 carbon atoms and
n stands for a number 2, 3 or 4,
Ar¹ stands for an o-phenylene radical which is optionally monosubstituted to tetrasubstituted by identical or different substituents and
Ar² stands for phenyl which is optionally monosubstituted to pentasubstituted by identical or different substituents, suitable phenyl or phenylene substituents for the radicals Ar¹ or Ar² in each case being: halogen, cyano, nitro, in each case straight-chain or branched alkyl, alkoxy or alkylthio each having 1 to 4 carbon atoms, in each case straight-chain or branched halogenoalkyl, halogenoalkoxy or halogenoalkylthio each having 1 to 4 carbon atoms and 1 to 9 identical or different halogen atoms,
with the proviso that at least one of the radicals Ar¹ or Ar² is substituted by halogenoalkoxy or halogenoalkylthio.

Particularly preferred compounds of the formula (I) are those in which
R stands for hydrogen, methyl or ethyl,
Q stands for a radical of the formula

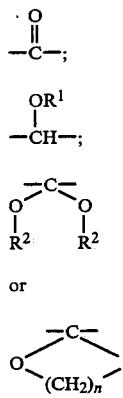

where
R¹ stands for hydrogen, methyl or ethyl,
R² stands for methyl or ethyl and
n stands for a number 2 or 3,
Ar¹ stands for an o-phenylene radical which is optionally monosubstituted, disubstituted or trisubstituted by identical or different substituents and
Ar² stands for phenyl which is optionally monosubstituted, disubstituted or trisubstituted by identical or different substituents, suitable phenyl or phenylene substituents for the radicals Ar¹ or Ar² in each case being: fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, difluoromethyl, difluorochloromethyl, dichlorofluoromethyl, trifluoromethoxy, trifluoromethylthio, difluoromethoxy, difluoromethylthio, difluorochloromethoxy, difluorochloromethylthio, dichlorofluoromethoxy or dichlorofluoromethylthio, with the proviso that at least one of the radicals Ar¹ or Ar² is substituted by trifluoromethoxy, trifluoromethylthio, difluoromethoxy, difluoromethylthio, difluorochloromethoxy, difluorochloromethylthio, dichlorofluoromethoxy or dichlorofluoromethylthio.

Very particularly preferred compounds of the formula (I) are those in which
R stands for hydrogen or methyl,
Q stands for a radical of the formula

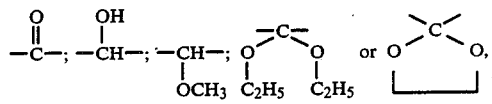

Ar¹ stands for an o-phenylene radical which is optionally monosubstituted, disubstituted or trisubstituted by identical or different substituents and
Ar² stands for phenyl which is optionally monosubstituted, disubstituted or trisubstituted by identical or different substituents, suitable phenyl or phenylene substituents for the radicals Ar¹ or Ar² in each case being: fluorine, chlorine, methyl, trifluoromethyl, trifluoromethoxy, difluoromethoxy or difluorochloromethoxy,
with the proviso that at least one of the radicals Ar¹ or Ar² is substituted by trifluoromethoxy, difluoromethoxy or difluorochloromethoxy.

Preferred compounds according to the invention are also addition products of acids and those pyridine-4-carboxylic acid anilides of the formula (I), in which the substituents R, Q, Ar¹ and Ar² have the meanings which have already been mentioned as preferred for these substituents.

The acids which can be adducted preferably include hydrohalic acids such as, for example, hydrochloric acid and hydrobromic acid, in particular hydrochloric acid, furthermore phosphoric acid, nitric acid, sulphuric acid, mono-, bi- and trifunctional carboxylic acids and hydroxycarboxylic acids such as, for example, acetic acid, maleic acid, succinic acid, fumaric acid, tartaric acid, citric acid, salicylic acid, sorbic acid and lactic acid, sulphonic acids such as, for example, p-toluenesulphonic acid and 1,5-naphthalenedisulphonic acid and also saccharin or thiosaccharin.

In addition, preferred compounds according to the invention are addition products of salts of metals of main groups II to IV and subgroups I and II and also IV to VIII and those pyridine-4-carboxylic acid anilides of the formula (I), in which the substituents R, Q, Ar¹ and Ar² have the meanings which have already been mentioned as preferred for these substituents. In this connection, salts of copper, zinc, manganese, magnesium, tin, iron and nickel are particularly preferred. Possible anions of these salts are those which are derived from those acids which lead to plant-tolerable addition products. In this connection, particularly preferred acids of this type are the hydrohalic acids such as, for example, hydrochloric acid and hydrobromic acid, nitric acid and sulphuric acid.

In detail, the following pyridine-4-carboxylic acid anilides of the general formula (I)

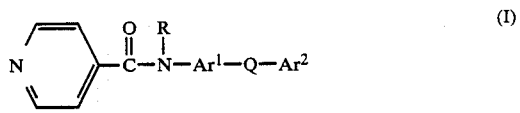

(I)

may be mentioned in addition to the compounds mentioned in the preparation examples:

| R | Ar¹ | Q | Ar² |
|---|---|---|---|
| H | 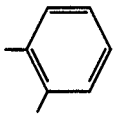 | $-\overset{O}{\underset{\|}{C}}-$ | —OCHF₂ |
| H | 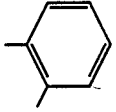 | $-\overset{O}{\underset{\|}{C}}-$ |  (OCF₃) |
| H | 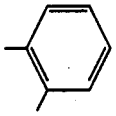 | $-\overset{O}{\underset{\|}{C}}-$ |  (F₃CO) |
| H | 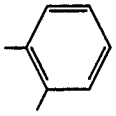 | $-\overset{O}{\underset{\|}{C}}-$ |  (OCHF₂) |
| H | 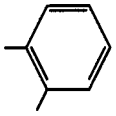 | $-\overset{O}{\underset{\|}{C}}-$ |  (F₂CHO) |
| H | 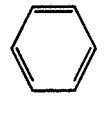 | $-\overset{O}{\underset{\|}{C}}-$ |  (Cl, OCF₃) |
| H | 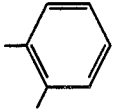 | $-\overset{O}{\underset{\|}{C}}-$ |  (CH₃, OCF₃) |
| H | 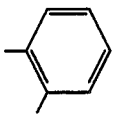 | $-\overset{O}{\underset{\|}{C}}-$ |  (Cl, OCF₃) |
| H | 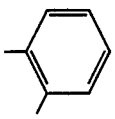 | $-\overset{O}{\underset{\|}{C}}-$ |  (OCF₃, Cl) |
| H | 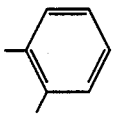 | $-\overset{O}{\underset{\|}{C}}-$ |  (CF₃, OCF₃) |
| H | 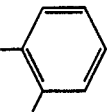 | $-\overset{O}{\underset{\|}{C}}-$ |  (OCHF₂, Cl) |

-continued
| R | Ar¹ | Q | Ar² |
|---|---|---|---|
| H | 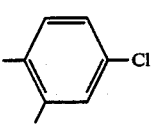 |  | 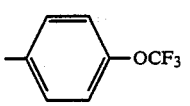 |
| H | 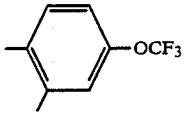 |  | 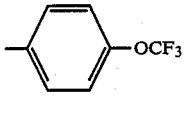 |
| H | 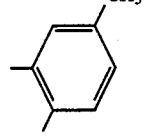 |  | 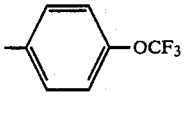 |
| H | 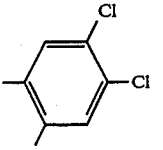 |  | 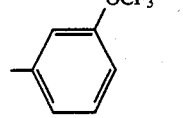 |
| H | 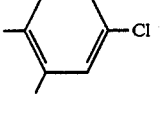 |  | 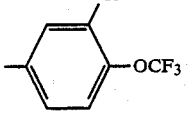 |
| H | 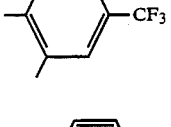 |  | 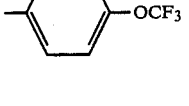 |
| H | 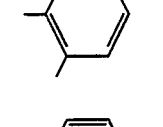 |  | 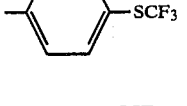 |
| H | 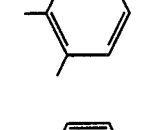 |  | 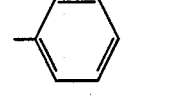 |
| CH₃ | 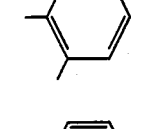 |  | 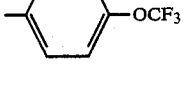 |
| CH₃ | 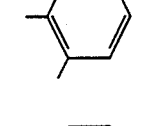 |  | 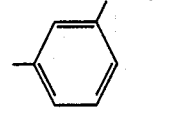 |
| CH₃ | 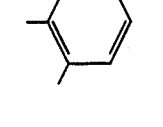 |  | 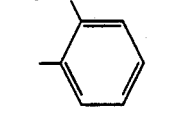 |

-continued

| R | Ar¹ | Q | Ar² |
|---|-----|---|-----|
| H | 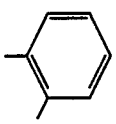 | $\underset{\underset{\text{CH}}{\mid}}{\text{OH}}$ |  4-OCHF₂ |
| H | 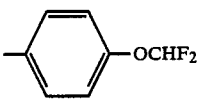 | $\underset{\underset{\text{CH}}{\mid}}{\text{OH}}$ | 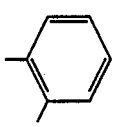 3-OCF₃ |
| H |  | $\underset{\underset{\text{CH}}{\mid}}{\text{OH}}$ | 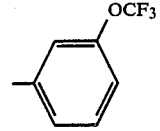 2-OCHF₂ |
| H | 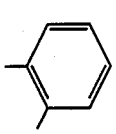 | $\underset{\underset{\text{CH}}{\mid}}{\text{OH}}$ |  3-OCHF₂ |
| H | 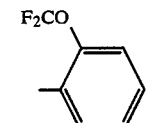 | $\underset{\underset{\text{CH}}{\mid}}{\text{OH}}$ | 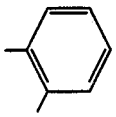 2-OCHF₂ |
| H |  | $\underset{\underset{\text{CH}}{\mid}}{\text{OH}}$ | 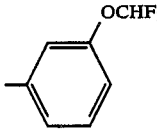 3-Cl, 4-OCF₃ |
| H | 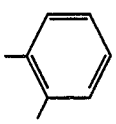 | $\underset{\underset{\text{CH}}{\mid}}{\text{OH}}$ |  3-CH₃, 4-OCF₃ |
| H | 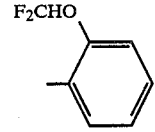 | $\underset{\underset{\text{CH}}{\mid}}{\text{OH}}$ | 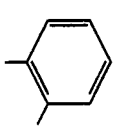 2-Cl, 4-OCF₃ |
| H |  | $\underset{\underset{\text{CH}}{\mid}}{\text{OH}}$ | 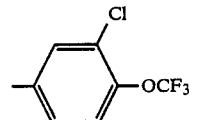 3-OCF₃, 4-Cl |
| H | 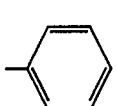 | $\underset{\underset{\text{CH}}{\mid}}{\text{OH}}$ |  2-CF₃, 4-OCF₃ |
| H | 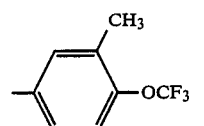 | $\underset{\underset{\text{CH}}{\mid}}{\text{OH}}$ | 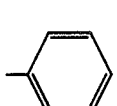 3-OCHF₂, 4-Cl |

-continued

| R | Ar¹ | Q | Ar² |
|---|---|---|---|
| H | 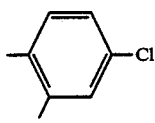 4-Cl | $\underset{\text{OH}}{-\text{CH}-}$ |  4-OCF₃ |
| H | 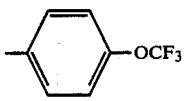 3-OCF₃ | $\underset{\text{OH}}{-\text{CH}-}$ | 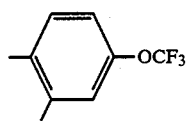 4-OCF₃ |
| H |  4-CH₃ | $\underset{\text{OH}}{-\text{CH}-}$ | 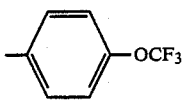 4-OCF₃ |
| H | 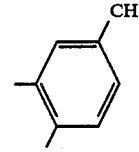 3,4-Cl₂ | $\underset{\text{OH}}{-\text{CH}-}$ |  3-OCF₃ |
| H | 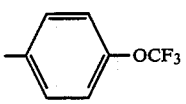 4-Cl | $\underset{\text{OH}}{-\text{CH}-}$ | 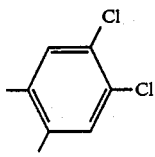 3-Cl, 4-OCF₃ |
| H |  4-CF₃ | $\underset{\text{OH}}{-\text{CH}-}$ | 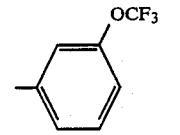 4-OCF₃ |
| H | 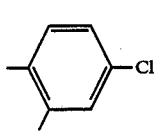 | $\underset{\text{OH}}{-\text{CH}-}$ |  4-SCF₃ |
| H | 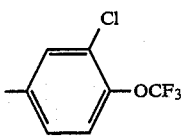 | $\underset{\text{OH}}{-\text{CH}-}$ | 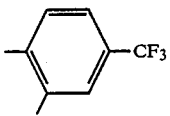 3-SCF₃ |
| CH₃ |  | $\underset{\text{OH}}{-\text{CH}-}$ | 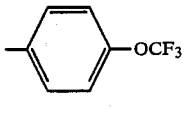 4-OCF₃ |
| CH₃ | 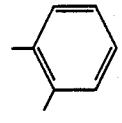 | $\underset{\text{OH}}{-\text{CH}-}$ |  3-OCF₃ |
| CH₃ | 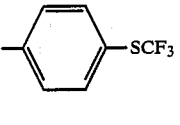 | $\underset{\text{OH}}{-\text{CH}-}$ | 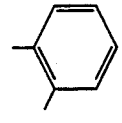 2-OCF₃ |

-continued
| R | Ar¹ | Q | Ar² |
|---|-----|---|-----|
| H | 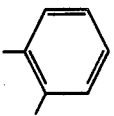 | 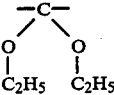 | 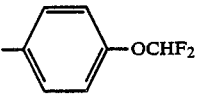 |
| H | 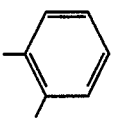 | 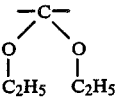 | 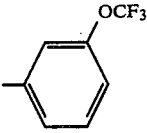 |
| H | 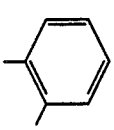 | 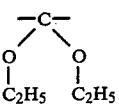 | 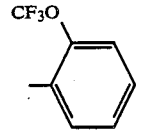 |
| H | 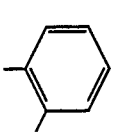 | 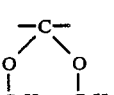 | 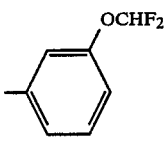 |
| H | 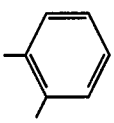 | 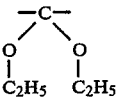 | 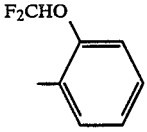 |
| H | 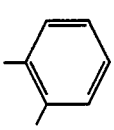 | 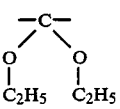 | 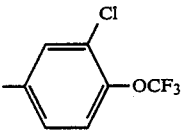 |
| H | 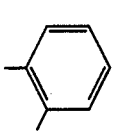 | 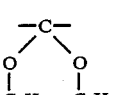 | 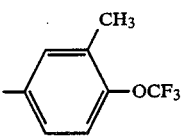 |
| H | 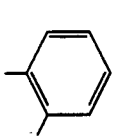 | 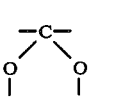 | 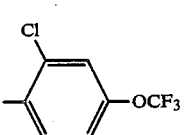 |
| H | 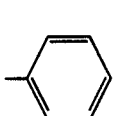 | 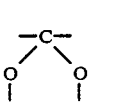 | 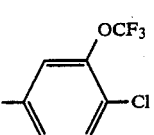 |
| H | 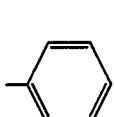 | 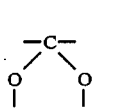 | 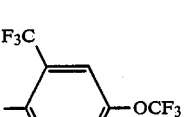 |
| H | 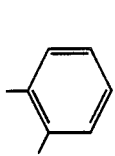 | 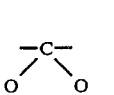 | 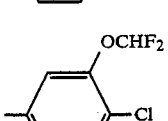 |

-continued

| R | Ar¹ | Q | Ar² |
|---|-----|---|-----|
| H | 4-Cl, 3-yl phenyl | $-C(OC_2H_5)_2-$ | 4-$OCF_3$ phenyl |
| H | 4-$OCF_3$, 3-yl phenyl | $-C(OC_2H_5)_2-$ | 4-$OCF_3$ phenyl |
| H | 3,4-diCl phenyl | $-C(OC_2H_5)_2-$ | 3-$OCF_3$ phenyl |
| H | 4-Cl, 3-yl phenyl | $-C(OC_2H_5)_2-$ | 3-Cl, 4-$OCF_3$ phenyl |
| H | 4-$CF_3$, 3-yl phenyl | $-C(OC_2H_5)_2-$ | 4-$OCF_3$ phenyl |
| H | 3-yl phenyl | $-C(OC_2H_5)_2-$ | 4-$OCHF_2$ phenyl |
| H | 3-yl phenyl | $-C(OC_2H_5)_2-$ | 4-$SCF_3$ phenyl |
| H | 3-yl phenyl | $-C(OC_2H_5)_2-$ | 4-$OCF_3$ phenyl |
| $CH_3$ | 3-yl phenyl | $-C(OC_2H_5)_2-$ | 4-$OCF_3$ phenyl |
| $CH_3$ | 3-yl phenyl | $-C(OC_2H_5)_2-$ | 3-$OCF_3$ phenyl |
| $CH_3$ | 3-yl phenyl | $-C(OC_2H_5)_2-$ | 2-$OCF_3$ phenyl |

-continued
| R | Ar¹ | Q | Ar² |
|---|---|---|---|
| H | 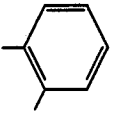 | 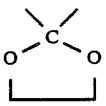 | 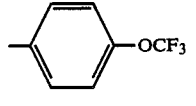 |
| H | 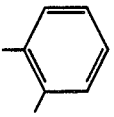 | 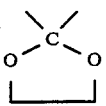 | 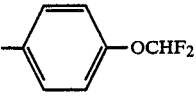 |
| H | 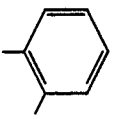 | 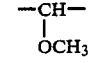 | 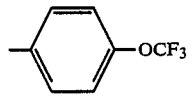 |
| H | 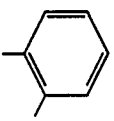 | 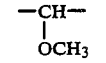 | 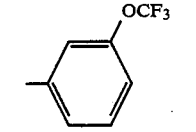 |
| H | 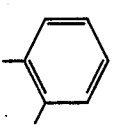 | 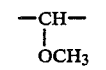 | 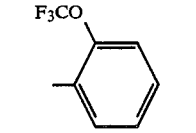 |
| H | 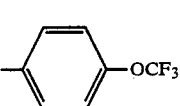 | 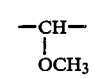 | 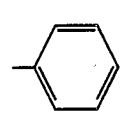 |
| H | 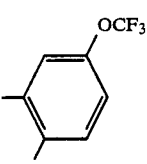 | 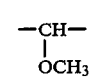 | 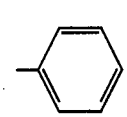 |
| H | 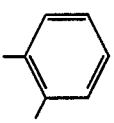 | 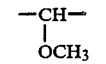 | 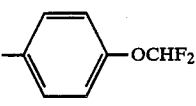 |
| H | 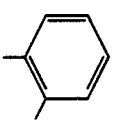 | 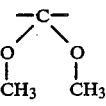 | 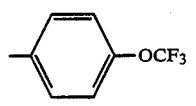 |
| H | 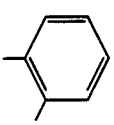 | 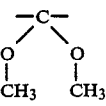 | 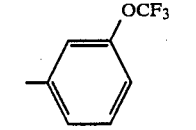 |
| H | 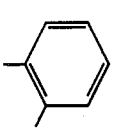 | 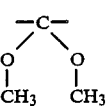 | 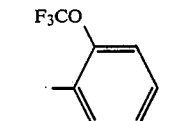 |

| R | Ar¹ | Q | Ar² |
|---|---|---|---|
| H | 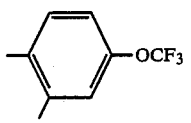 (dimethyl-substituted phenyl with OCF₃) | —C(OCH₃)(OCH₃)— | 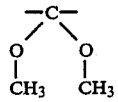 (phenyl) |
| H | 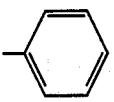 (dimethyl-substituted phenyl with OCF₃) | —C(OCH₃)(OCH₃)— | 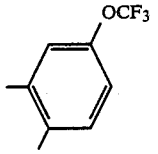 (phenyl) |
| H | 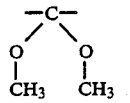 (dimethyl-substituted phenyl) | —C(OCH₃)(OCH₃)— | 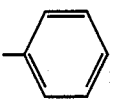 (phenyl-OCHF₂) |

If, for example, pyridine-4-carbonyl chloride hydrochloride and 2-amino-4'-trifluoromethoxybenzophenone are used as starting materials, then the course of the reaction of process (a) according to the invention can be represented by the following equation:

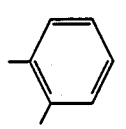

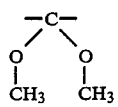

If, for example, N-[2-(4-trifluoromethoxybenzoyl)-phenyl]-pyridine-4-carboxamide is used as a starting compound and sodium borohydride as a reductant, then the course of the reaction of process (b) according to the invention can be represented by the following equation:

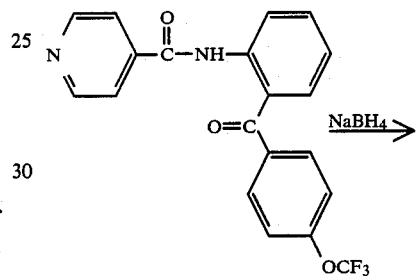

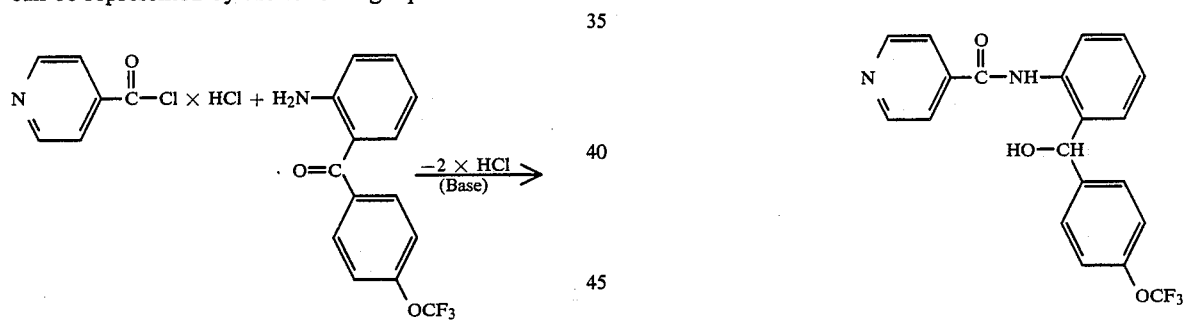

If, for example, N-[2-(4-trifluoromethoxy-α-hydroxybenzyl)-phenyl]-pyridine-4-carboxamide and dimethyl sulphate are used as starting materials, then the course of the reaction of process (c) according to the invention can be represented by the following equation:

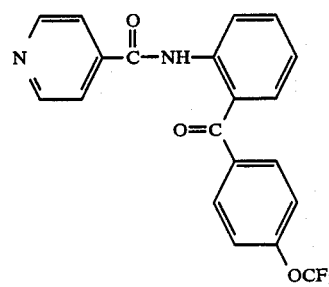 + CH₃O—SO₂—OCH₃

$$\xrightarrow[\text{(Base)}]{-CH_3O-SO_3H}$$

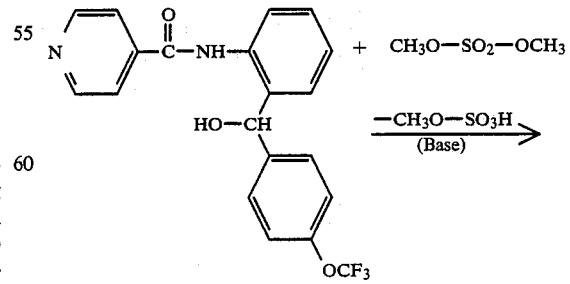

-continued

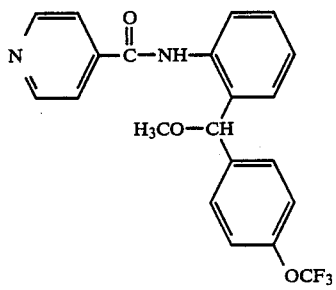

If, for example, N-[2-(4-trifluoromethoxybenzoyl)-phenyl]-pyridine-4-carboxamide and ethanol are used as starting materials, then the course of the reaction of process (d) according to the invention can be represented by the following equation:

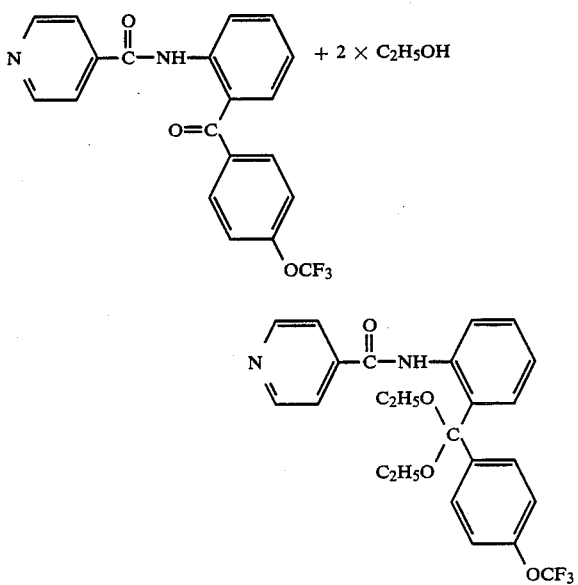

Formula (II) provides a definition of the pyridine-4-carbonyl halide hydrochlorides required as starting materials for carrying out process (a) according to the invention.

The pyridine-4-carbonyl halide hydrochlorides of the formula (II) are known (compare, for example, J. Org. Chem. 47, 2633–2637 [1982]; U.S. Pat. No. 3,813,400).

Formula (III) provides a general definition of the aminobenzophenones furthermore required as starting materials for carrying out process (a) according to the invention. In this formula (III), R, $Ar^1$ and $Ar^2$ preferably stand for those radicals which have already been mentioned as preferred for these substituents in connection with the description of the substances of the formula (I) according to the invention.

Some of the aminobenzophenones of the formula (III) are known (compare, for example, Khim.-Farm. Zh. 15, 28–31 [1981] or CA 96: 97 054p; Khim. Geterotsikl. Soedin. 1975, 268–272 or CA 82: 170 851p; Fiziol. Akt. Veshchestva 14, 36–39 [1982] or CA 99: 88 147f; FR.M. FR 7666 of 09.02.1970 or CA 76: 12 70 289) or obtainable in analogy to known processes, for example when anilines of the formula (VI)

$$H_2N-Ar^1-H \qquad (VI)$$

in which $Ar^1$ has the abovementioned meaning, are reacted with benzonitriles of the formula (VII)

$$NC-Ar^2 \qquad (VII)$$

in which $Ar^2$ has the abovementioned meaning, if appropriate in the presence of a diluent, such as, for example, dichloromethane or 1,2-dichloroethane, and in the presence of a suitable reaction auxiliary, such as, for example, a mixture of boron trichloride and aluminium trichloride, at temperatures between −5° C. and +120° C. (compare with this also J. Amer. chem. Soc. 100, 4842 [1978] and the preparation examples).

Anilines of the formula (VI) and benzonitriles of the formula (VII) are generally known compounds of organic chemistry (compare, for example, U.S. Pat. No. 4,434,182; EP No. 65,447; DE-OS (German Published Specification) No. 2,812,169; Zh. Obshch. Khim. 39, 206–210 [1969] or CA 70: 96 318d; J. org. Chem. 44, 2907–2910 [1979]).

Formula (Ia) provides a general definition of the pyridine-4-carboxylic acid anilides required as starting materials for carrying out processes (b) and (d) according to the invention. In this formula (Ia), R, $Ar^1$ and $Ar^2$ preferably stand for those radicals which have already been mentioned as preferred for these substituents in connection with the description of the substances of the formula (I) according to the invention.

The pyridine-4-carboxylic acid anilides of the formula (Ia) are compounds according to the invention and obtainable with the aid of process (a) according to the invention.

Formula (Ib) provides a general definition of the pyridine-4-carboxylic acid anilides required as starting materials for carrying out process (c) according to the invention. In this formula (Ib), R, $Ar^1$ and $Ar^2$ preferably stand for those radicals which have already been mentioned as preferred for these substituents in connection with the description of the substances of the formula (I) according to the invention.

The pyridine-4-carboxylic acid anilides of the formula (Ib) are compounds according to the invention and obtainable with the aid of process (b) according to the invention.

Formula (IV) provides a general definition of the alkylating agents required as starting materials for carrying out process (c) according to the invention. In this formula (IV), $R^{1-1}$ preferably stands for straight-chain or branched alkyl having 1 to 4 carbon atoms, in particular for methyl or ethyl.

E stands for a leaving group customary in alkylating agents, preferably for an optionally substituted alkyl-, alkoxy- or arylsulphonyloxy radical, such as, for example, a methoxysulphonyloxy radical, an ethoxysulphonyloxy radical or a p-toluenesulphonyloxy radical.

The alkylating agents of the formula (IV) are generally known compounds of organic chemistry.

Formula (V) provides a general definition of the alcohols or diols furthermore required as starting materials for carrying out process (d) according to the invention. In this formula (V), $R^3$ preferably stands for straight-chain or branched alkyl having 1 to 4 carbon atoms, in particular for methyl or ethyl or for a radical $-(CH_2)_n-OH$, where n preferably stands for a number 2, 3 or 4, in particular for a number 2 or 3.

The alcohols or diols of the formula (V) are generally known compounds of organic chemistry.

Suitable diluents for carrying out process (a) according to the invention are inert organic solvents. In particular, these include aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran or ethylene glycol dimethyl ether or ethylene glycol diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate or bases, such as pyridine.

Process (a) according to the invention is preferably carried out in the presence of a suitable acid-binding agent. Those suitable are all customary inorganic or organic bases. These include, for example, alkali metal hydroxides, such as sodium hydroxide or potassium hydroxide, alkali metal carbonates, such as sodium carbonate, potassium carbonate or sodium hydrogen carbonate, and tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

The reaction temperatures can be varied within a relatively wide range when carrying out process (a) according to the invention. In general, the reaction is carried out at temperatures between 0° C. and 150° C., preferably at temperatures between 20° C. and 120° C.

For carrying out process (a) according to the invention, in general 0.8 to 3.0 moles, preferably 1.0 to 1.5 moles, of aminobenzophenone of the formula (III) and, if appropriate, 1.0 to 20.0 moles, preferably 1.0 to 10.0 moles, of acid-binding agent is employed per mole of pyridine-4-carbonyl halide hydrochloride of the formula (III). The reaction is carried out, and the reaction products are worked up and isolated according to generally customary methods (compare also the preparation examples).

Suitable reductants for carrying out process (b) according to the invention are all reductants customary for carbonyl group reductions of that type. Complex hydrides, such as sodium borohydride, sodium cyanoborohydride or lithium borohydride, optionally in the presence of calcium chloride, by means of which complex calcium borohydrides can also be formed in the reaction mixture, are used with particular advantage.

Suitable diluents for carrying out process (b) according to the invention are inert organic solvents. Ethers, such as diethyl ether, dioxane, tetrahydrofuran or ethylene glycol dimethyl ether or ethylene glycol diethyl ether or alcohols, such as methanol, ethanol, n- or i-propanol, if appropriate also mixed with water, are preferably used.

The reaction temperatures can be varied within a relatively wide range when carrying out process (b) according to the invention. In general, the reaction is carried out at temperatures between −100° C. and +200° C., preferably at temperatures between −50° C. and +50° C.

For carrying out process (b) according to the invention, in general 0.1 to 1.5 moles, preferably 0.25 to 1.0 mole, of complex hydride and, if appropriate, 0.1 to 1.5 moles, preferably 0.25 to 1.0 mole, of calcium chloride are employed per mole of pyridine-4-carboxylic acid anilide of the formula (Ia). The reaction is carried out, and the reaction products are worked up and isolated according to generally customary methods (compare also the preparation examples).

Suitable diluents for carrying out process (c) according to the invention are inert organic solvents. In particular, these include aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran or ethylene glycol dimethyl ether or ethylene glycol diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate or sulphoxides, such as dimethyl sulphoxide.

Process (c) according to the invention can optionally also be carried out in a two-phase system, such as, for example, water/toluene or water/dichloromethane, if appropriate in the presence of a phase-transfer catalyst. Examples of such catalysts which may be mentioned are: tetrabutylammonium iodide, tetrabutylammonium bromide, tributyl-methylphosphonium bromide, trimethyl-$C_{13}/C_{15}$-alkylammonium chloride, dibenzyl-dimethylammonium ethylsulphate, dimethyl-$C_{12}/C_{14}$-alkyl-benzylammonium chloride, tetrabutylammonium hydroxide, 15-crown-5, 18-crown-6, triethylbenzylammonium chloride and trimethylbenzylammonium chloride.

Process (c) according to the invention is preferably carried out in the presence of a suitable reaction auxiliary. Those which are suitable are all customarily utilizable inorganic and organic bases. Alkali metal hydrides, hydroxides, amides, alkoxides, carbonates or hydrogen carbonates, such as, for example, sodium hydride, sodium amide, sodium hydroxide, sodium methoxide, sodium ethoxide, potassium t-butoxide, sodium carbonate or sodium hydrogen carbonate or else tertiary amines, such as, for example, triethylamine, N,N-dimethylaniline, pyridine, N,N-dimethylaminopyridine, diazabicyclooctane (DABCO), diazabicyclononene (DBN) or diazabicycloundecene (DBU) are preferably used.

The reaction temperatures can be varied within a relatively wide range when carrying out process (c) according to the invention. In general, the reaction is carried out at temperatures between −50° C. and 200° C., preferably at temperatures between 0° C. and 100° C.

For carrying out process (c) according to the invention, in general 1.0 to 5.0 moles, preferably 1.0 to 1.5 moles, of alkylating agent of the formula (IV) and optionally 1.0 to 3.0 moles, preferably 1.0 to 1.2 moles, of reaction auxiliary are employed per mole of pyridine-4-carboxylic acid anilide of the formula (Ib). The reaction is carried out, and the reaction products are worked up and isolated by generally customary methods (compare, for example, JP No. 60/204,764).

Suitable diluents for carrying out process (d) according to the invention are inert organic solvents. In particular, these include aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform, carbon tetrachloride or ethers, such as diethyl ether, dioxane, tetrahydrofuran or ethylene glycol dimethyl ether or ethylene glycol diethyl ether.

Process (d) according to the invention is preferably carried out in the presence of a suitable reaction auxiliary. Those which are suitable are preferably all customarily utilizable inorganic or organic acids or other customary catalysts. Dilute aqueous or concentrated mineral acids, such as hydrochloric acid, sulphuric acid or phosphoric acid, organic sulphonic acids, such as methanesulphonic acid or p-toluenesulphonic acid or acid chlorides, such as, for example, thionyl chloride, if appropriate in the presence of an acid-binding agent, such as pyridine or triethylamine, are used with particular advantage.

The reaction temperatures can be varied within a relatively wide range when carrying out process (d) according to the invention. In general, the reaction is carried out at temperatures between 0° C. and 200° C., preferably at temperatures between 20° C. and 150° C.

For carrying out process (d) according to the invention, in general 1.0 to 30.0 moles, preferably 2.0 to 5.0 moles, of alcohol or 1.0 to 5.0 moles of diol of the formula (V) and, if appropriate, 0.01 to 2.0 moles, preferably 0.1 to 1.0 mole, of reaction auxiliary are employed per mole of pyridine-4-carboxylic acid anilide of the formula (Ia). The reaction is carried out, and the reaction products are worked up and isolated by generally customary methods.

The acid addition salts of the compounds of the formula (I) can be obtained in a simple manner by customary salt formation methods, such as, for example, by dissolving a compound of the formula (I) in a suitable inert solvent and adding the acid, such as, for example, hydrochloric acid, and can be isolated in a known manner, for example by filtering off, and, if appropriate, can be purified by washing with an inert organic solvent.

The metal salt complexes of compounds of the formula (I) can be obtained in a simple manner by customary methods, thus, for example, by dissolving the metal salt in alcohol, for example ethanol and adding to the compound of the formula (I). Metal salt complexes can be isolated in a known manner, for example by filtering off and can be purified, if appropriate, by recrystallization.

The active compounds according to the invention have a strong action against pests and can be employed practically for combating undesired harmful organisms. The active compounds are suitable for use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation: Pythium species, such as, for example, *Pythium ultimum*; Phytophthora species, such as, for example, *Phytophthora infestans*; Pseudoperonospora species, such as, for example, *Pseudoperonospora humuli* or *Pseudoperonospora cubensis*; Plasmopara species, such as, for example, *Plasmopara viticola*; Peronospora species, such as, for example, *Peronospora pisi* or *P. brassicae*; Erysiphe species, such as, for example, *Erysiphe graminis*; Sphaerotheca species, such as, for example, *Sphaerotheca fuliginea*; Podosphaera species, such as, for example, *Podosphaera leucotricha*; Venturia species, such as, for example, *Venturia inaequalis*; Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus*; Puccinia species, such as, for example, *Puccinia recondita*; Tilletia species, such as, for example, *Tilletia caries*; Ustilago species, such as, for example, *Ustilago nuda* or *Ustilago avenae*; Pellicularia species, such as, for example, *Pellicularia sasakii*; Pyricularia species, such as, for example, *Pyricularia oryzae*; Fusarium species, such as, for example, *Fusarium culmorum*; Botrytis species, such as, for example, *Botrytis cinerea*; Septoria species, such as, for example, *Septoria nodorum*; Leptosphaeria species, such as, for example, *Leptosphaeria nodorum*; Cercospora species, such as, for example, *Cercospora canescens*; Alternaria species, such as, for example, *Alternaria brassicae* and Pseudocercosporella species, such as, for example, *Pseudocercosporella herpotrichoides*.

The good toleration, by plants, of the active compounds, at the concentrations required for combating plant diseases, permits treatment of above-ground parts of plants, of vegetative propagation stock and seeds, and of the soil.

The active compounds according to the invention can thus be used with particularly good effect for combating cereal diseases, such as, for example, against the pathogen of true cereal mildew (*Erysiphe graminis*) or against the pathogen of glume blotch of wheat (*Leptosphaeria nodorum*) or against the pathogen of net blotch of barley (*Pyrenophora teres*) or for combating diseases in fruit and vegetable cultivation, such as, for example, against the pathogen of apple scab (*Venturia inaequalis*) or against the pathogen of apple mildew (*Podosphaera leucotricha*) or against the pathogen of cucumber mildew (*Sphaerotheca fuliginae*).

Depending on their particular physical and/or chemical properties, the active compounds can be converted to the customary formulations, such as solutions, emulsions, suspensions, powders, foams, pastes, granules, aerosols, very fine capsules in polymeric substances and in coating compositions for seeds, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colourants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

Preparation examples

EXAMPLE 1

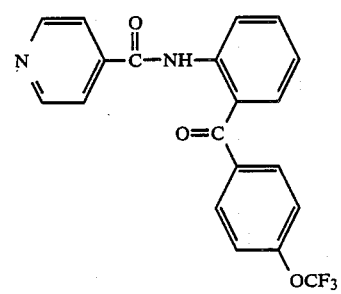

(process a)

9.8 g (0.055 mol) of pyridine-4-carbonyl chloride hydrochloride are added in portions with stirring to 14 g (0.05 mol) of 2-(4-trifluoromethoxybenzoyl)-aniline in 200 ml of pyridine, the mixture is subsequently heated to 50° C. for 4 hours and concentrated in vacuo, the residue is taken up in water, extracted a number of times using ethyl acetate, the combined organic phases are washed with water and dried over sodium sulphate, and the solvent is removed in vacuo.

13.6 g (71% of theory) of N-[2-(4-trifluoromethoxybenzoyl)-phenyl]-pyridine-4-carboxamide of melting point 112°–114° C. are obtained.

Preparation of the starting compound

Example III-1

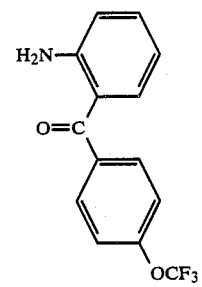

First 45.4 ml (0.5 mol) of aniline and 500 ml of 1,2-dichloroethane and subsequently, in alternating portions, 102.8 g (0.55 mol) of 4-trifluoromethoxybenzonitrile (compare, for example, J. org. Chem. 44, 2907–2910 [1979]) and 66.6 g (0.5 mol) of aluminum chloride are added at 0° C. to 10° C. with stirring and ice cooling to 500 ml (0.5 mol) of 1-normal boron trichloride solution in dichloromethane. After completion of the addition, the mixture is diluted using a further 500 ml of 1,2-dichloroethane, dichloromethane is distilled off and the mixture is heated for 6 hours with reflux of the 1,2-dichloroethane (83° C.). It is subsequently cooled to room temperature, 400 ml of 2-normal hydrochloric acid and a further 500 ml of 1,2-dichloroethane are added and the mixture is heated for a further 3 hours at reflux temperature. After cooling, 98 g (70% of theory) of 2-(4-trifluoromethoxybenzoyl)-aniline are obtained as a solid by filtering off and drying.

$^1$H-NMR (CDCl$_3$/tetramethylsilane): δ=7.2–7.4; 7.5–7.6; 7.7–7.8 ppm.

EXAMPLE 2

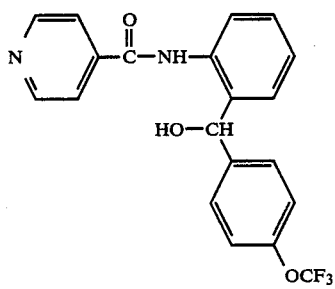

(process b)

1 g (0.026 mol) of sodium borohydride is added to 10 g (0.026 mol) of N-[2-(4-trifluoromethoxybenzoyl)-phenyl]-pyridine-4-carboxamide in 200 ml of methanol and the mixture is stirred for 15 hours at room temperature. For working up, it is concentrated in vacuo, water is added to the residue and it is extracted a number of times using ethyl acetate, and the combined ethyl acetate phases are dried over sodium sulphate and freed from solvent in vacuo.

9.4 g (93% of theory) of N-[2-(4-trifluoromethoxy-α-hydroxybenzyl)-phenyl]-pyridine-4-carboxamide of melting point 65? C. are obtained.

USE EXAMPLES

The compounds shown below were employed as comparison substances in the following use examples:

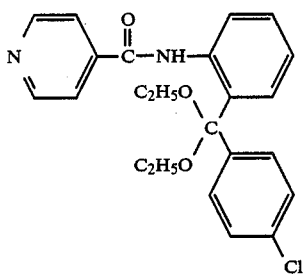

(A)

N-[4-chloro-2-(4-chloro-α,α-diethoxybenzyl)-phenyl]-pyridine-4-carboxamide
(known from EP 122,410)

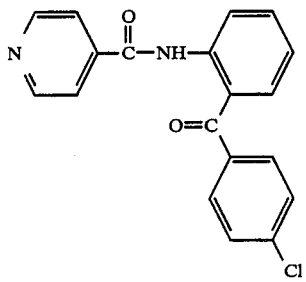

(B)

N-[2-(4-chlorobenzoyl)-phenyl]-pyridine-4-carboxamide
(known from Jp 60/23,364)

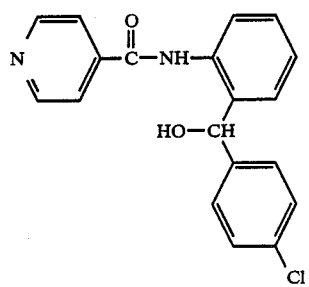

(C)

N-[2-(4-chloro-α-hydroxybenzyl)-phenyl]-pyridine-4-carboxamide
(known from Jp 60/32,703)

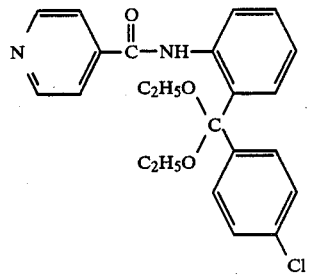

(D)

N-[2-(4-chloro-α,α-diethoxybenzyl)-phenyl]-pyridine-4-carboxamide
(known from EP 122,410)

EXAMPLE A

Erysiphe test (barley)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis* f.sp. hordei.

The plants are placed in a greenhouse at a temperature of about 20° C. and a relative atmospheric humidity of about 80%, in order to promote the development of powdery mildew pustules.

Evaluation is carried out 7 days after the inoculation.

In this test, a clearly superior activity compared with the prior art is shown, for example, by the compounds according to the preparation Examples 1 and 2.

EXAMPLE B

*Leptosphaeria nodorum* test (wheat)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Leptosphaeria nodorum*. The plants remain for 48 hours in an incubation cabin at 20° C. and 100% relative atmospheric humidity.

The plants are placed in a greenhouse at a temperature of about with the proviso that at least one of the radicals $Ar^1$ or $Ar^2$ is substituted by halogenoalkoxy or halogenoalkylthio, or an acid addition salt or metal salt complex thereof.

2. A pyridine-4-carboxylic acid anilide according to claim 1, in which

R stands for hydrogen, methyl or ethyl, $R^1$ stands for hydrogen, methyl or ethyl, $Ar^1$ stands for an o-phenylene radical which is optionally monosubstituted or disubstituted by identical or different substituents and $Ar^2$ stands for phenyl which is optionally monosubstituted or disubstituted by identical or different substituents, when present the phenyl or phenylene substituents for the radicals $Ar^1$ or $Ar^2$ in each case being selected from the group consisting of fluorine, chlorine, bromine, methyl, ethyl, n- or i-propyl, n-, i-, s- or t-butyl, methoxy, ethoxy, n- or i-propoxy, methylthio, trifluoromethyl, trifluoromethoxy, trifluoromethylthio, difluoromethyl, difluoromethoxy, difluoromethylthio, difluorochloromethyl, difluorochloromethoxy, difluorochloromethylthio, dichlorofluoromethyl, dichlorofluoromethoxy and dichlorofluoromethylthio, with the proviso that at least one of the radicals $Ar^1$ or $Ar^2$ is substituted by trifluoromethoxy, trifluoromethylthio, difluoromethoxy, difluoromethylthio, difluorochloromethoxy, difluorochloromethylthio, dichlorofluoromethoxy or dichlorofluoromethylthio, or an acid addition salt or metal salt complex thereof.

3. A pyridine-4-carboxylic acid anilide according to claim 1, in which

R stands for hydrogen or methyl,

Q stands for a radical of the formula

or

$Ar^1$ stands for an o-phenylene radical which is optionally monosubstituted or disubstituted by identical or different substituents and $Ar^2$ stands for phenyl which is optionally monosubstituted or disubstituted by identical or different substituents, when present the phenyl or phenylene substituents for the radicals $Ar^1$ or $Ar^2$ in each case being selected from the group consisting of fluorine, chlorine, methyl, trifluoromethyl, trifluoromethoxy, difluoromethoxy and difluorochloromethoxy with the proviso that at least one of the radicals $Ar^1$ or $Ar^2$ is substituted by trifluoromethoxy, difluoromethoxy or difluorochloromethoxy, or an acid addition salt or metal salt complex thereof.

4. A compound according to claim 1, wherein such compound is N-(2-(4-trifluoromethoxybenzoyl)-phenyl)-pyridine-4-carboxamide of the formula

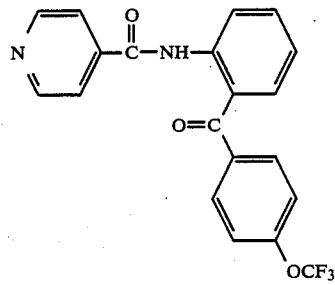

or an acid addition salt or metal salt complex thereof.

5. A compound according to claim 1, wherein such compound is N-(2-(4-trifluoromethoxy-α-hydrobenzyl)-phenyl)-pyridine-4-carboxamide of the formula

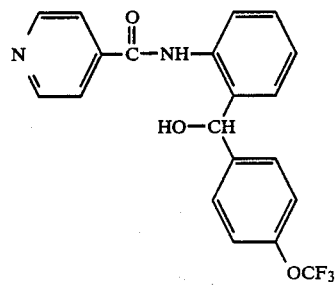

or an acid addition salt or metal salt complex thereof.

6. A fungicidal composition comprising a fungicidally effective amount of a compound, salt or complex according to claim 1 and a diluent.

7. A method of combating fungi which comprises applying to such fungi or to a fungus habitat a fungicidally effective amount of a compound, salt or complex according to claim 1.

8. The method according to claim 7, wherein such compound is
N-(2-(4-trifluoromethoxybenzoyl)-phenyl)-pyridine-4-carboxamide or
N-(2-(4-trifluoromethoxy-α-hydrobenzyl)-phenyl)-pyridine-4-carboxamide,
or an acid addition salt or metal salt complex thereof.

* * * * *